United States Patent [19]  [11] 4,293,555
Christensen et al. [45] * Oct. 6, 1981

[54] 6- AND 6,6-DISUBSTITUTED-2-SUBSTITUTED-OXAPEN-2-EM-3-CARBOXYLIC ACIDS

[75] Inventors: Burton G. Christensen, Scotch Plains; Frank P. DiNinno, Old Bridge, both of N.J.

[73] Assignee: Merck & Co., Inc., Rahway, N.J.

[*] Notice: The portion of the term of this patent subsequent to Oct. 30, 1996, has been disclaimed.

[21] Appl. No.: 83,721

[22] Filed: Oct. 10, 1979

Related U.S. Application Data

[63] Continuation-in-part of Ser. No. 30,970, Apr. 17, 1979, abandoned, and Ser. No. 30,788, Apr. 17, 1979, abandoned, which is a continuation of Ser. No. 865,277, Dec. 28, 1977, abandoned, and Ser. No. 865,109, Dec. 28, 1977, abandoned.

[51] Int. Cl.³ ................ C07D 498/04; C07D 205/08; A61K 31/42; C07D 409/06
[52] U.S. Cl. ........................... 424/263; 260/326.47; 260/245.2 R; 260/245.3; 260/239 A; 260/245.4; 260/347.4; 546/256; 546/270; 546/328; 560/193; 560/196; 560/146; 560/9; 549/72; 424/272; 548/253; 548/125
[58] Field of Search ................ 424/263, 272; 546/270, 546/256; 260/245.3

[56] References Cited

U.S. PATENT DOCUMENTS 4,172,895 10/1974 Christensen et al. ............ 260/245.3

OTHER PUBLICATIONS

Cherry, Chem. Abs. 88, 190807f (1978).

Primary Examiner—Mark L. Berch
Attorney, Agent, or Firm—Hesna J. Pfeiffer; Julian S. Levitt

[57] ABSTRACT

Disclosed are 6- and 6,6-disubstituted-2-substituted-oxapen-2-em-3-carboxylic acids of the following structure:

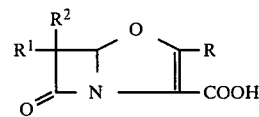

wherein: $R^1$ and $R^2$ are independently selected from hydrogen, alkyl, alkoxyl, aralkyl, aryl, heterocyclyl and heterocyclylalkyl; R is selected from hydrogen, —OR, —SR, —NR$_2$, alkyl, aryl, aralkyl, heterocyclyl, or heterocyclylalkyl. Such compounds and their pharmaceutically acceptable salt, and ester derivatives are useful as antibiotics. Also disclosed are processes for the preparation of such compounds, pharmaceutical compositions comprising such compounds and methods of treatment comprising administering such compounds and compositions when an antibiotic effect is indicated.

5 Claims, No Drawings

6- AND 6,6-DISUBSTITUTED-2-SUBSTITUTED-OXAPEN-2-EM-3-CARBOXYLIC ACIDS

STATUS OF RELATED APPLICATIONS

This application is a continuation-in-part of U.S. Ser. No. 30,970, filed Apr. 17, 1979, now abandoned, and U.S. Ser. No. 30,788, filed Apr. 17, 1979, now abandoned, which respectively, were continuations of U.S. Ser. No. 865,277, filed Dec. 28, 1977, now abandoned, and U.S. Ser. No. 865,109, filed Dec. 28, 1977, now abandoned.

BACKGROUND OF THE INVENTION

This invention relates to 6- and 6,6-disubstituted-2-substituted-oxapen-2-em-3-carboxylic acids and their pharmaceutically acceptable salts and esters, which compounds are useful as antibiotics and which may be represented by the following generic structural formula (I):

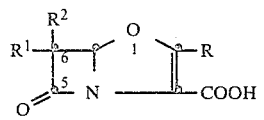

wherein: $R^1$ and $R^2$ are, inter alia, independently selected from hydrogen, substituted and unsubstituted: alkyl, alkoxyl, aryl, aralkyl, heterocyclyl and heterocyclylalkyl; and R is, inter alia, selected from hydrogen, —OR, —SR, —NR$_2$, and substituted and unsubstituted: alkyl, aryl, aralkyl, heterocyclyl and heterocyclylalkyl; wherein the substituents on $R^1$, $R^2$ or R are selected from amino, mono-, di- and trialkylamino, hydroxyl, alkoxyl, mercapto, alkylthio, arylthio, such as phenylthio, sulfamoyl, amidino, guanidino, nitro, chloro, bromo, fluoro, cyano and carboxyl.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacterial such as *E. coli,* Pseudomonas, *Proteus morganii,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

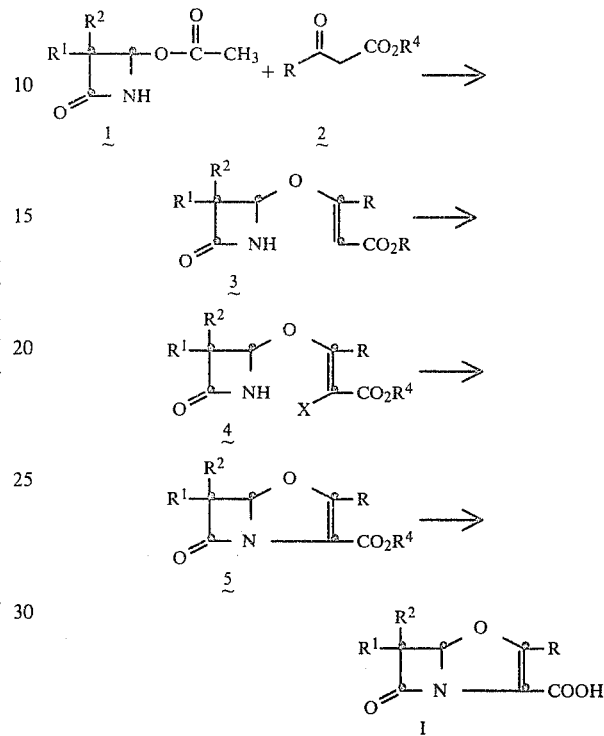

In words relative to the above diagram, the starting azetidinone 1 is treated with a malonic acid derivative (2) in the presence of base such as sodium hydride, aluminum isopropoxide, Al[OCH(CH$_3$)$_2$]$_3$, lithium diisopropylamine and the like in a solvent such as dimethoxyethane, tetrahydrofuran (THF), dimethylformamide and the like at a temperature of from 0° to 22° C. for from 1 to 96 hours to provide the eeco-lactam 3. $R^4$ is a readily removable carboxyl blocking group such as p-nitrobenzyl, o-nitrobenzyl, 2,2,2-trichoroethyl, t-butyldimethylsilyl or the like. Halogenation of 3 yields 4 wherein X is halo, such as chloro or bromo. Suitable halogenating agents include N-chlorosuccinimide, N-bromosuccinimide, N-bromoacetamide and the like; and the reaction 3→4 is conducted in the presence of a halogenating agent of choice in a solvent such as THF, benzene, benzene/ether and the like at a temperature of from 0° to 60° C. for from 0.5 to 24 hours. Cyclization of 4 to provide 5 is accomplished by treating 4 with a strong base such as lithium diisopropylamide, lithium hexamethylsilazide, lithium tetramethylpiperidide or the like in a solvent such as THF, hexamethylphosphoramide, dimethoxyethane or the like in the presence of cuprous iodide, cuprous bromide-dimethyl sulfide complex, cuprous iodide-tri-n-butylphosphine complex or the like at a temperature of from −78° to 22° C. for from 0.5 to 18 hours. The carboxyl protected intermediate 5 is deblocked to provide I. When the preferred blocking groups, $R^4$ are employed such as p-nitrobenzyl or trichloroethyl, the deblocking reaction may be accomplished by hydrogenation or zinc mediated reduction according to well-known procedures. A representative deblocking procedure comprises treating 5 in a solvent such as ethylacetate under hydrogen (1–40 atmosphere) at a temperature of 0° to 25° C. for from 0.25 to 2 hours in the presence of a hydrogenation catalyst such as 10% Pd/C, 5% Pd/BaCO₃, 5% Pt/C or the like.

The starting azetidinone material 1 may conveniently be prepared by the following scheme:

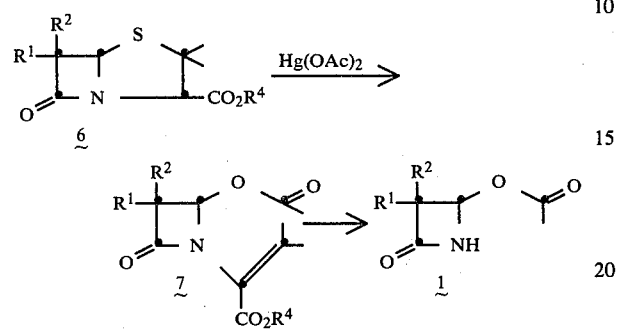

wherein R¹, R² and R⁴ are as defined above; the preparation of starting material 6 is given below in the Examples Section.

In words relative to the above diagram, starting material 6 is cleaved with mercuric acetate (Hg(OAc)₂) in acetic acid solution at a temperature of from 22° C. to 110° C. for from 0.25 hours to provide the acetoxy lactam 7. Relative to these reactions, R⁴ is a readily removable carboxyl protecting group such as methyl, benzyl, trichloroethyl or the like. Removal of the isopropylidene ester function is accomplished by treating 7 with potassium permanganate, osmium tetroxide or the like in a solvent such as aqueous pyridine, aqueous acetone or the like at a temperature of 0° to 22° C. for from 0.25 to 2 hours, to provide azetidinone 1. Analogous procedures are known in the literature; see, for example: E. G. Brain, et al., *J. Chem. Soc.*, Perkin I, 447 (1976); R. J. Stoodley and N. R. Whitehouse, Ibib., 32 (1973).

Starting material 2 in the above-described synthesis, may conveniently be prepared in a variety of ways. One preferred method, when the ultimate 2-substituent (Structure I) is —SR, is shown in the following scheme:

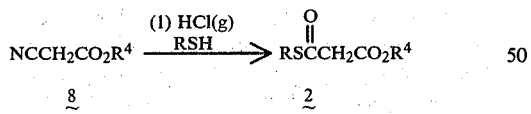

In words relative to the above diagram, the cyanoacetic acid ester 8 is treated with gaseous hydrogen chloride in a solvent such as benzene, diethylether, tetrahydrofuran or the like in the presence of a mercaptan (RSH) at a temperature of from 0° C. to 25° C. for from 0.25 to 1 hour. The resulting mixture is stirred at a temperature of from 0° to 80° C. for from 8 to 96 hours. The precipitated formed is collected by filtration, redissolved in dimethylsulfoxide, dimethylformamidine or the like, and treated with aqueous hydrochloric acid, aqueus trifluoroacetic acid or the like at a temperature of from 25° to 80° C. for from 0.25 to 24 hours to afford 2; R and R⁴ are as previously defined.

The following list representatively illustrates suitable starting materials 2. Such reagents are employed as described in the above procedure to provide species bearing a preferred substituent at the 2-position.

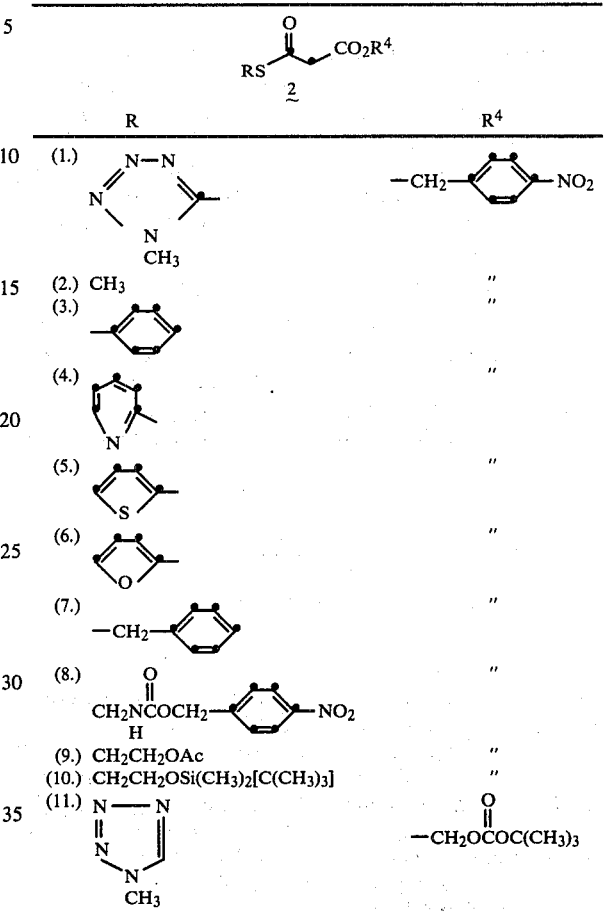

When starting material 2 in the above-described synthesis, provides the 2-substituent as -R, it may be prepared by known literature procedures.

The following list representatively illustrates suitable starting materials 2. Such reagents are employed as described in the above procedure to provide species bearing a preferred substituent at the 2-position.

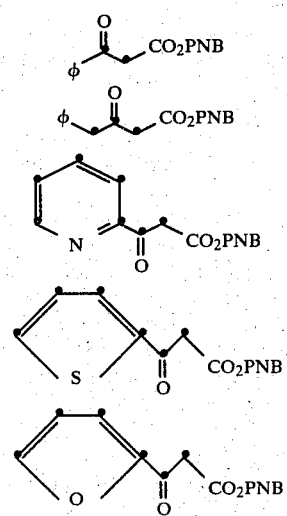

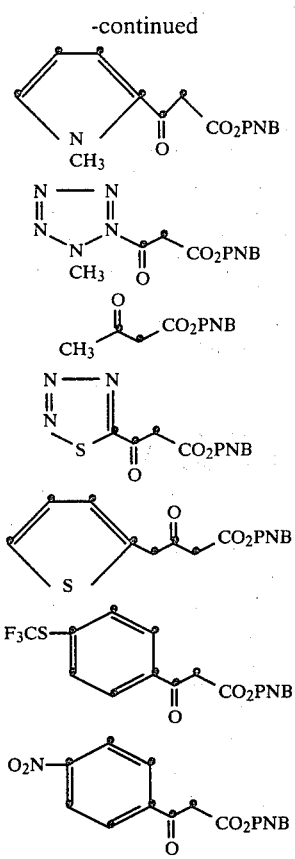

(PNB = P-nitrobenzyl)
(φ = phenyl)

In the generic representation of the compounds of the present invention (I):

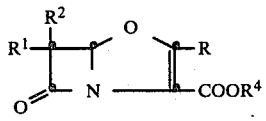

The preferred values for R are: hydrogen; substituted and unsubstituted: —OR, —SR, —NR₂ (R is defined herein), alkyl having 1-6 carbon atoms, aryl such as phenyl, aralkyl wherein the aryl moiety is preferably phenyl and the alkyl has 1-6 carbon atoms such as benzyl, phenethyl and the like, heterocycyl or heterocyclyalkyl wherein the alkyl has 1-3 carbon atoms and the heterocyclic ring comprises 4-6 atoms, up to 4 of which may be selected from oxygen, sulfur and nitrogen; and wherein the chain or nuclear substituent on R is selected from: amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano and carboxyl; the alkyl moieties of the above-recited substituents have 1-6 carbon atoms.

The preferred ester moieties, R⁴, (see 5, above) used as carboxyl protecting groups are those wherein R² is benzyl, p-nitrobenzyl, o-nitrobenzyl, t-butyl, bromo-t-butyl, t-butyl-dimethylsilyl, trimethylsilyl, trichloroethyl; R² may also represent, in addition to hydrogen, pharmaceutically acceptable ester moieties such as pivaloyloxymethyl, allyl, methallyl, (2-methylthio)-ethyl, or 3-buten-1-yl; and pharmaceutically acceptable salt cations.

R¹ and R² are independently selected from the group consisting of: hydrogen, substituted and unsubstituted: alkyl, alkenyl, and alkynyl, having from 1-10 carbon atoms; cycloalkyl, cycloalkyalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the linear chain has 1-6 carbon atoms; heteroaryl, heteroaralkyl, heterocyclyl and heterocyclylalkyl wherein the substituent or substituents relative to the above-named radicals are selected from the group consisting of: amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano and carboxy, and wherein the hetero atom or atoms in the above-anmed heterocyclic moieties are selected from the group consisting of 1-4 oxygen, nitrogen or sulphur atoms; and wherein the alkyl moieties of the above-recited substituents have 1-6 carbon atoms.

The most preferred embodiments of the present invention (I) are those wherein R¹ is hydrogen and R² is hydroxymethyl, 1'-hydroxyethyl, 1'-hydroxy-3-phenylpropyl, 1'-hydroxy-3-phenyl-3-carboxypropyl, 1'-hydroxy-2',2',2'-trifluoroethyl; R¹ is methoxyl, and R² is all of above; R¹ and R² are hydrogen; R³ is hydrogen, phenyl, methyl, 2'-thienyl, 2'-pyridyl, benzyl, p-methoxyphenyl or SR wherein R is as described above and is especially: aminomethyl and aminoethyl.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, loweralkanolamines, di-loweralkanolamines, lower alkylenediamines, N,N-diaralkyl lower alkylenediamines, aralkylamines, amino substituted lower alkanols, N,N-di-loweralkalamino substituted lower alkanols, amino-, polyamino and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

Salts of the amino group carried of I are also contemplated. Such pharmaceutically acceptable acid addition salts are derived from organic and inorganic acids such as HCl, HBr, citric, tartaric and the like.

The salts can be mono-salts such as the mono-sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel 6- and 6,6-disubstituted-2-substituted oxapen-2-em-3-carboxylic acids of the present invention are valuable antimicrobial substances which are active against various gram-positive and gram-negative pathogens. Thus, the free acid and especially the salts thereof such as amino and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus*. The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacterial on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitble vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All temperatures are in +C.

EXAMPLE 1

Preparation of Starting Material 6

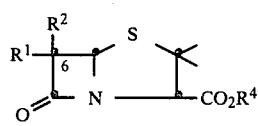

wherein $R^1$, $R^2$ and $R^4$ are as defined above. In general, the compounds 6 are prepared according to the method of DiNinno, et al., [F. DiNinno, T. R. Beattie, and B. G. Christensen, J. Org. Chem., 42, 2960 (1977)] which is summarized in Schemes I and II:

Scheme I

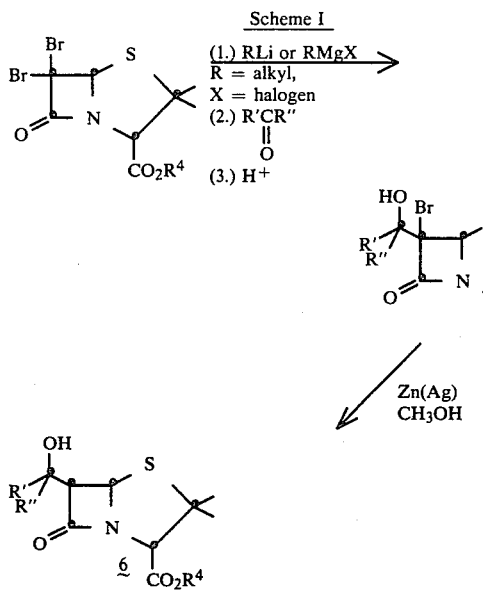

Scheme II

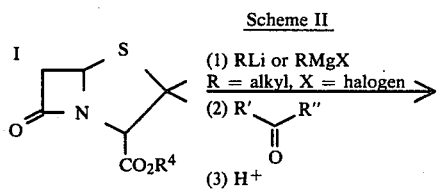

wherein R' and R" may be hydrogen, alkyl, aralkyl, heterocyclyl and heterocyclylalkyl.

The substituents at ring position 6 correspond in this Example I to the generally defined substituent $R^1$ and $R^2$ of Structure I, above. Thus, radicals such as

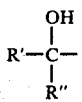

and —OR (below) encountered here in this Example 1 at position 6 are but convenient specific demonstrations of the generic radicals $R^1$ and $R^2$ as defined above for Structure I, the ultimate compounds of the present invention.

It is to be noted that the above reaction scheme is regio-specific for the 6-position and that there are no criticalities of reaction parameters other than those set forth above and elaborated upon in the following specific examples. It should be further noted that the above-described procedure provides all embodiments of the present invention except those wherein one of the 6-substituents is alkoxyl such as methoxyl, for example; in that event, the above procedure is modified as illustrated in the following scheme:

Scheme III:

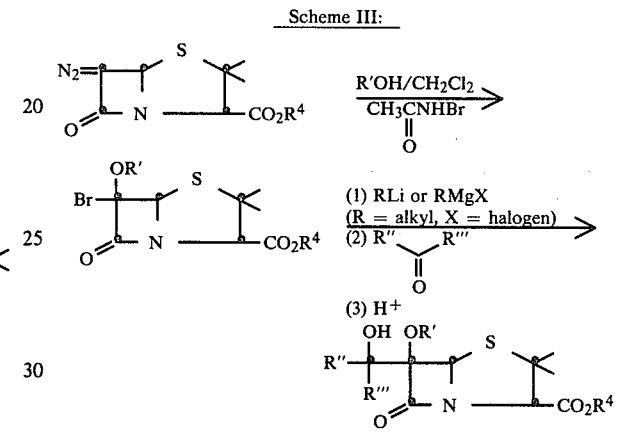

In Scheme III, the diazo starting material is available to the art; see for example: Hauser, et al., Helv. Chim. Acta. 50, 1327 (1967). Typically the first step of the reaction is conducted in a solvent medium such as R'OH or a mixture of R'OH and a solvent such as $CH_2Cl_2$, acetonitrile, benzene or the like containing 1 to about 3 equivalents of a brominating agent such as N-bromoacetamide, N-bromosuccinimide, or the like; typically the reaction is conducted at from about 0° to about 50° C. for from a few minutes to 12 hours. The resulting 6-bromo-6-substituted species are known [Cama, et al., J. Amer. Chem. Soc., 95,1408 (1972)] as is the above described process; the 6-bromo-6-substituted species is then treated with a base (1.0 to 1.5 equivalents) such as an organo-metallic base, for example, n-butyl lithium, methyl magnesium bromide, or the like in a solvent such as diethyl ether, tetrahydrofuran, dimethoxyethane or the like at a temperature of from −80° C. to about 0° C.; and thereafter adding, as above-described, the reagent of choice

to give the desired final product.

EXAMPLE 2

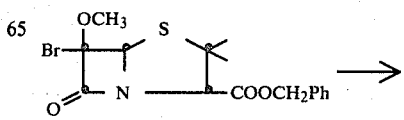

-continued

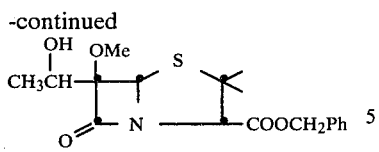

6

Preparation of benzyl-6-methoxy-6-(1-hydroxyethyl)-penicillanate (6)

To a stirred solution of 90.8 mg. (0.2 mmol) of benzyl-6-methoxy-6-bromopenicillanate [prepared according to L. D. Cama, W. J. Leanza, T. R. Beattie, and B. G. Christensen, *J. Amer. Chem. Soc.*, 95, 1408 (1972)] in 5 ml of dry THF at −78° under a nitrogen atmosphere is added dropwise 69 μl (0.2 mmol) of 2.9 M ethereal methylmagesium bromide. The mixture is stirred at −78° under nitrogen for 0.5 hours and 57 μl (1 mmol) of neat acetaldehyde is added. The resulting mixture is stirred at −78° for 0.5 hours and 0.5 ml. of saturated, aqueous NH$_4$Cl solution is added. The mixture is partitioned between Et$_2$O and H$_2$O and the organic phase is separated, dried (MgSO$_4$), filtered, and evaporated. Purification by plate layer chromotography affords benzyl-6-methoxy-6-(1-hydroxyethyl)penicillanate (6).

EXAMPLE 3

Following the foregoing Examples and text, the following useful starting materials 6 for the practice of the present invention are obtained by analogy.

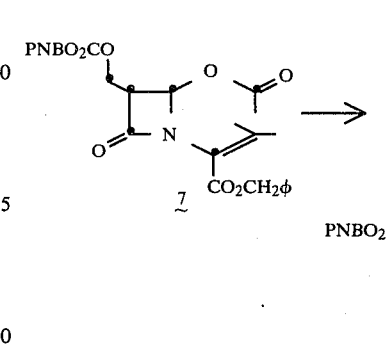

| Compound | R' | R'' | R |
|---|---|---|---|
| (1.) | H | H | H |
| (2.) | φCH$_2$CH$_2$—<br>φ = phenyl | H | H |
| (3.) | H | H | OCH$_3$ |
| (4.) | CF$_3$ | H | H |
| (5.) | NH$_2$<br>\|<br>φCHCH$_2$ | H | H |
| (6.) | CH$_3$ | H | OCH$_3$ |
| (7.) | H | CF$_3$ | H |
| (8.) | HOOC—⌬—CH$_2$CH$_2$ | CH$_3$ | H |
| (9.) | ⌬—CH$_2$CH$_2$CH$_2$ | H | H |
| (10.) | CH$_3$ | H | H |
| (11.) | CH$_3$ | CH$_3$ | H |
| (12.) | φCH$_2$ | H | H |
| (13.) | CH$_3$CH$_2$ | H | OCH$_3$ |
| (14.) | φCH<br>\|<br>NH$_2$ | H | OCH$_3$ |

EXAMPLE 4

Preparation of Azetidinone 1

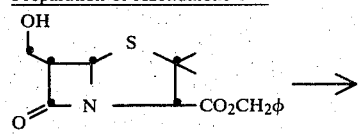

-continued

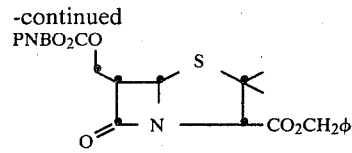

6

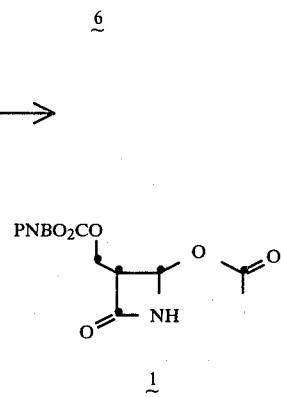

PNB = p-nitrobenzyl
φ = phenyl

Step A, Preparation of 6

To a stirred solution of 215 mg. (0.6 mmol) of benzyl-6-[1'-hydroxymethyl]penicillanate and 276 mg (0.13 mmol) p-nitrobenzylchloroformate in 5 ml dry methylene chloride at 0° C. is added in one portion solid 4-dimethylaminopyridine (156 mg., 0.13 mmole). The mixture is stirred at 0° C. under a nitrogen atmosphere for 2 min. and allowed to warm over 28 min. The mixture is poured into ice-H$_2$O and extracted with CH$_2$Cl$_2$. The organic phase is separated and washed successively with cold, dilute, aqueous HCl and saturated NaCl (aq.). After drying with MgSO$_4$, the filtered solution is evaporated and dried in vacuo. Purification by plate layer chromatography provides 6.

Step B

Preparation of 7

A stirred mixture of 180 mg (0.36 mmol) of 6 and 232 mg. (0.73 mmol) Hg(OAc)$_2$ (mercuric acetate) in 7 ml glacial HOAc (acetic acid) is heated at 90° C. for 1.5 hour under a nitrogen atmosphere. The cooled mixture is filtered through supercel, washing thoroughly with CH$_2$Cl$_2$. The filtrate is diluted with H$_2$O and is neutralized with solid NaHCO$_2$. The mixture is extracted thoroughly with CH$_2$Cl$_2$ and the combined extracts are washed successively with saturated NaHCO$_3$ (aq.) and saturated NaCl (aq.). After drying with MgSO$_4$, the filtered solution is evaporated and the residue so obtained is purified by plate layer chromatography to provide 7.

Step C

Preparation of 1

To a stirred solution of 136.8 mg (0.26 mmol) of azetidinone 7 in 3.5 ml of 8:1 (CH$_3$)$_2$CO—H$_2$O and 1 drop of pH 7 0.1 N phosphate buffer at room temperature (25° C.) is added 40.6 mg (0.26 mmol) of solid KMnO$_4$. The mixture is stirred under a nitrogen atmosphere at 25° C. for 8 min. After this time, 40.6 mg (0.26 mmol) of additional KMnO$_4$ is added and the mixture is stirred further for 45 min. The reaction mixture is diluted with EtOAc (ethylacetate) and treated with cold, aqueous Na$_2$S$_2$O$_3$ until the violet coloration of KMnO$_4$ is no longer apparent. The mixture is filtered through celite and is washed well with EtOAc. The filtrate is washed with saturated NaCl (aq.), dried (MgSO₄), filtered, and evaporated. Purification of the residue by plate layer chromatography gives 1.

EXAMPLE 5

Following the procedure of Example 4 the following 3- and 3,3-disubstituted-4-acetoxy azetidinones 1 are prepared by analogy.

| Compound | R¹ | R² |
|---|---|---|
| a. | —CH₂OCCH₂—⟨C₆H₄⟩—NO₂ (O=) | H |
| b. | OCO₂PNB / —CHCH₂CH₂φ | H |
| c. | OCO₂PNB / —CHCH₂CHφ / CO₂PNB | H |
| d. | OCO₂PNB / —C—CF₃ | H |
| e. | OCO₂PNB / —CH₂CHφ / CO₂PNB | OCH₃ |
| f. | OCO₂PNB / —CCH₃ | OCH₃ |
| g. | OCO₂PNB / —CH₂ | OCH₃ |
| h. | H | H |
| i. | OCO₂PNB / [CH-CH=CH-CH=CH-S side chain] | H |
| j. | OCO₂PNB / —CHCH₂CHφ / HNCO₂PNB | H |

PNB = p-nitrobenzyl
φ = phenyl

EXAMPLE 6

Preparation of
6-[1′-hydroxymethyl]-2-aminoethylthio-oxapen-2-em-3′-carboxylic acid (I)

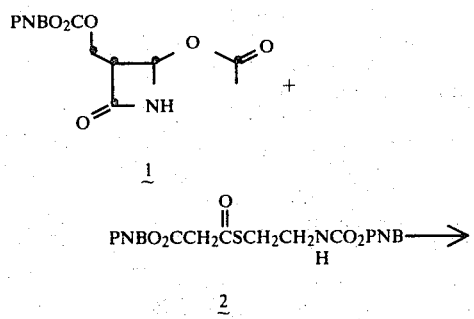

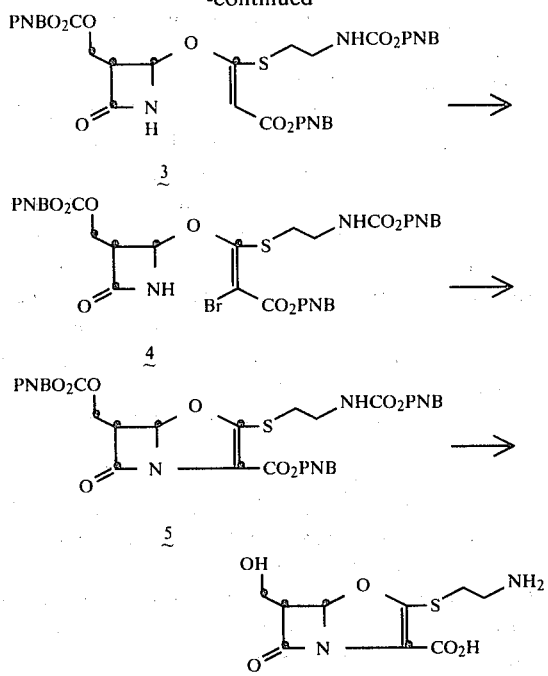

Step A:
Preparation of 2

$$\underset{H}{PNBO_2CCH_2\overset{O}{\overset{\|}{C}}SCH_2CH_2NCO_2PNB} \quad 2$$

To a stirred solution of 3.77 g (17.2 mmol) of p-nitrobenzylcyanoacetate and 4.0 g (15.6 mmol) of N-p-nitrocbzcysteamine in 40 ml dry benzene at 25° under a nitrogen atmosphere is introduced a stream of HCl(g) for 7 min. The reaction mixture is cooled on an ice water bath and the introduction of HCl(g) continued for 3 min. The ice water bath is removed and the mixture is stirred magnetically for 24 hours. After this time, the solution is removed from the separated solid with the aid of a filter stick and the solid is washed with dry benzene (2×40 ml) in the same manner. The solid is dried in vacuo in the reaction flask, then dissolved in dry dimethylsulfoxide (DMSO) at 25° C. To the stirred solution is added 2.5 N aqueous HCl and the mixture is stirred at 25° C. for 3 hr. The mixture is poured into diethyl ether and ice-water. The organic phase is separated and washed with water (4x) and saturated sodium chloride (aqueous) solution. The organic phase is dried (MgSO₄), filtered, and evaporated. Purification by column chromatography yields 2: NMR(CDCl₃)δ: 3.0–3.6 (4H, m), 3.7(2H, s), 5.17 (2H, s), 5.27 (2H, s), 7.47(4H, d, J=8 Hz), 8.17(4H, d, J=8 Hz); m/e 341 (M⁺−136), 256, 239, 209, 195, 165, 153, 136.

Step B:
Preparation of Seco-Lactam 3

To a stirred mixture of 60.8 mg (0.18 mmol) of azetidinones 1 and 85.9 mg (0.18 mmol) of 2 in 1.5 ml of dry THF at 25° C. is added in one portion 50.5 mg (0.25 mmol) of solid aluminum isoproproxide [Al(O—<)₃]. The mixture is stirred at 25° C. under N₂ for 6.0 hr. and is then partitioned between EtOAc and a cold, aqueous solution of dilute HCl-tartaric acid mixture. The EtOAc phase is separated and is washed with saturated NaCl- (aq.), dried (MgSO₄), filtered, and evaporated. Purification by plate layer chromatography provides 3.

Step C:

Preparation of Bromide 4

To a stirred solution of lactam 3 (64.2 mg, 0.085 mmol) and 15.1 mg (0.085 mmol) HMPA (hexamethylphosphoramide in 2.0 ml dry THF (tetrahydrofuran) at 25° C. is added in one portion 16.5 mg (0.093 mmol) solid NBS (N-bromosuccinimide). The mixture is stirred at 25° C. under N₂ for 15 hr. and evaporated. The residue is partitioned between EtOAc and H₂O and the EtOAc phase is separated. It is further washed with H₂O (2×) and saturated NaCl (aq.), then dried (MgSO₄), filtered, and evaporated. Purification by repetitive plate layer chromatography affords 4.

Step D:

Preparation of Oxapenem 5

To a stirred mixture of 33.4 mg (0.04 mmol) of bromide 4 and 28 mg (0.14 mmol) of CuBr.S(CH₃)₂ in 5 ml dry THF at −78° C. under N₂ is added 2 ml of a cold, freshly prepared solution of lithium diisopropylamide, LiN⟨⟩₂, [generated at 0°/20 min. with 5 mg (0.05 mmol) NH⟨⟩₂ (diisopropylamide) and 19 μl of 2.4 M buLi (butyllithium)]. The mixture is stirred over the following temperature ranges for the times indicated: −78° to −74° (40 min.); −74° to −68° (30 min.); −68° to −57° (30 min.); −57° to −41° (20 min.); −41° to −26° (20 min.); −26° to −20° (28 min.); −20° to −13° (38 min.); −15° to −9° (53 min.); −10° to −5° (18 min.); and −5° to 0° (18 min.). The mixture is then treated at 0° with 1 ml of saturated NH₄Cl (aq.) and diluted with Et₂O/H₂O. The organic phase is separated and washed further with aqueous NH₄Cl and saturated NaCl (aq.). The organic layer is dried (MgSO₄), filtered, and evaporated. The residue is purified by plate layer chromatography to afford 5.

Step E:

Preparation of Oxapenem I

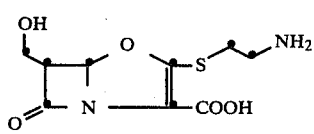

I

To 5.2 mg 5 (Step D, above) is added 0.60 ml dioxane, 0.05 ml ethanol, 0.35 ml deionized water and 0.01 ml of 1.0 M K₂HPO₄. To the resultant clear solution is added 5 mg of 10% Pd/C. The suspension is flushed with N₂, then 5–6 times alternately with 50 psi H₂ and vacuum. Finally, it is shaken under a 50 psi H₂ atmosphere for 30–40 min. After centrifugation, the Pd/C is washed and centrifuged 2–3× with 0.5 ml portions of deionized water. The combined centrifugates are extracted 5×1–2 ml ether. Residual ether is removed under vacuum and the aqueous solution applied to an XAD-2 column (20×140 mm). Fractions of 100 drops (6–7 ml) are collected, with continuous UV monitoring, by elution with deionized water. The chosen fractions are combined and lyophilized to provide I.

EXAMPLE 7

Preparation of

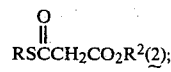

R² = CH₃, R = PNB (p-nitrobenzyl)

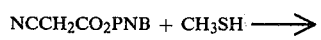

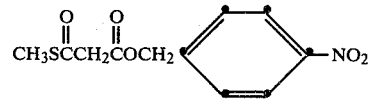

2

To a stirred mixture of 11.0 g (0.05 mol) of p-nitrobenzylcyanoacetate and 3.72 g (0.078 mol) methylmercaptan in 200 ml of sodium dried benzene at 25° C. is introduced a stream of HCl(g) until 1.85 g (0.05 mmol) is added. The mixture is then stirred at 25° C. under nitrogen atmosphere for 74.5 hrs. The solution is decanted away from the separated solid and the moist precipitate is dissolved in 50 ml of dimethyl sulfoxide. To the stirred solution is added 2.5 N aqueous hydrochloric acid and the mixture is stirred further 1.0 hr. The mixture is poured into diethylether-ice water and the organic phase is separated. The organic layer is washed with water (4×) and saturated aqueous sodium chloride solution, then dried (MgSO₄), filtered, and evaporated. Purification by column chromatography affords 2: IR(CHCl₃) 1750 and 1680 cm⁻¹; NMR (CDCl₃) δ: 2.4 (s, 3H), 3.7 (s, 2H), 5.3 (s, 2H), 7.5 (d, J=8 Hz, 2H), 8.23 (d, J=8 Hz, 2H); m/e 269 (M+), 222, 153 136.

EXAMPLE 8

Preparation of

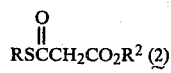

O
∥
(R=CH₂CH₂OCCH₃; R² = PNB)

To a stirred mixture of 6.78 g (5.6 mmol) of 2-acetoxyethyl mercaptan and 11.0 g (5 mmol) p-nitrobenzylcyanoacetate in 100 ml of dry benzene is introduced 3.0 g (8.1 mmol) of hydrogen chloride gas. The mixture is stirred under N₂ at RT (25° C.) for 42 hours after which time the solution is decanted away from the oily mass. The mass is washed twice with dry benzene by decantation. The oil is dissolved in 20 ml of dry dimethylformamide and is treated with 10 ml of water at 25° C. for 16 hours. The mixture is poured into Et₂O-H₂O and the organic phase is separated and washed further with water (4×) and saturated sodium chloride (aq.). The organic layer is then dried, filtered, and evaporated. Purification by column chromatography on silica gel affords 2; NMR (CDCl₃) δ: 2.03 (s, 3H), 3.57 (t, J=6 Hz, 2H), 3.7 (s, 2H), 4.3 (t, J=6 Hz, 2H), 5.33 (s, 2H), 7.53 (d, J=8 Hz, 2H), 8.2 (d, J=8 Hz, 2H).

EXAMPLE 9

Following the procedure described in the foregoing text and Examples, the following starting reagents 2 necessary for the preparation of the compounds of the present invention are representatively obtained by analogy.

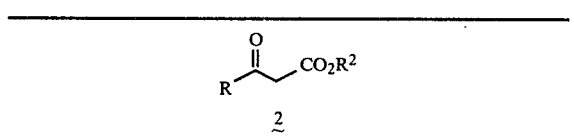

| Compound | R | R² |
|---|---|---|
| 1. | -S-[N-methyltetrazolyl ring] | -CH₂-[phenyl]-NO₂ |
| 2. | -SCH₃ | " |
| 3. | -S-[pyrrole] | " |
| 4. | -S-[pyridine] | " |
| 5. | -S-[thiophene] | " |
| 6. | -S-[furan] | " |
| 7. | -SCH₂-[furan] | " |
| 8. | -SCH₂NHCOOCH₂-[phenyl]-NO₂ | " |
| 9. | -SCH₂CH₂OCCH₃ (O) | " |
| 10. | -SCH₂CH₂OSi(CH₃)₂C(CH₃)₃ | " |
| 11. | phenyl | benzyl- |
| 12. | methyl | p-nitrobenzyl |
| 13. | 2-furyl | " |
| 14. | 2-thienyl | " |
| 15. | 2-pyridyl | " |
| 16. | 2-N-methyltetrazolyl | " |
| 17. | benzyl | " |
| 18. | 2-thiatriazolyl | " |
| 19. | p-trifluoromethylthiophenyl | " |
| 20. | p-nitrophenyl | " |
| 21. | 2-thienylmethyl | " |

EXAMPLE 10

Preparation of Seco-lactam 3: R₁=R₂=H, R₃=CH₃,

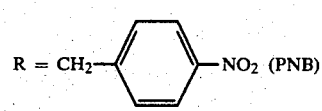

Reaction:

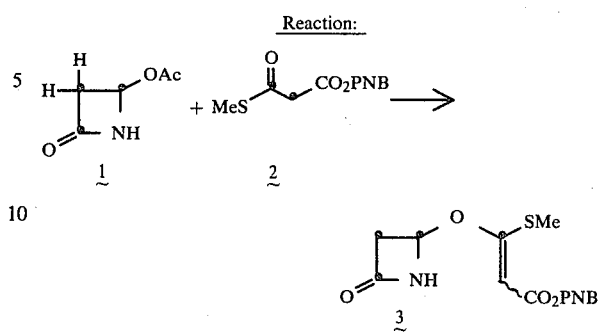

A mixture of 504 mg (3.9 mmol) of acetoxyazetidinone and 887.7 mg (3.3 mmol) of 2 in 20 ml tetrahydrofuran is cooled briefly on an ice/H₂O bath under Argon atmosphere and 694.5 mg (3.4 mmol) of aluminum isopropoxide is added. The mixture is stirred cold for 10 mins and the ice/H₂O bath is then removed. The mixture is stirred further for 67 hrs. The reaction is diluted with EtOAc and washed with saturated NaCl(aq.), cold, dilute aqueous HCl and the organic phase is separated, dried over MgSO₄, filtered, and evaporated. Purification by plate layer chromatography affords 3.

EXAMPLE 11

Preparation of secolactam 3

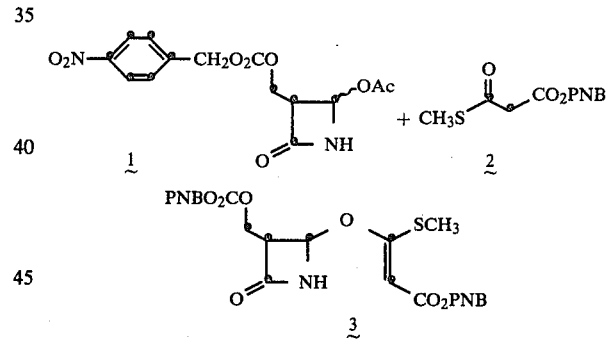

PNB = p-nitrobenzyl

To a stirred mixture of 67.6 mg (0.2 mmol) of azetidinones 1 and 53.8 mg (0.2 mmol) of 2 in 2 ml of dry tetrahydrofuran (THF) at 25° C. is added 57.2 mg (0.28 mmol) of solid aluminum isopropoxide. The mixture is stirred at 25° C. under nitrogen atmosphere for 50 hours and is then partitioned between ethylacetate and cold, dilute aqueous HCl. The EtOAc phase is separated, washed with brine, dried with MgSO₄, filtered, and evaporated. Purification by plate layer chromatography provides secolactam 3.

EXAMPLE 12

Following the procedures described in the foregoing Examples and text, the following secolactams 3 are prepared by analogy.

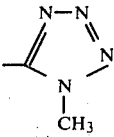

| Compound | R¹ | R | R² |
|---|---|---|---|
| a. | $-CH_2OCCH_2$ (with =O) | $-CH_2CH_3$ | H |
| b. | $\underset{\underset{-CHCH_2CH_2\phi}{\mid}}{OCO_2PNB}$ | (1-methyl-tetrazol-5-yl) | H |
| c. | $\underset{\underset{\underset{CO_2PNB}{\mid}}{-CHCH_2CH\phi}}{OCO_2PNB}$ | phenyl | H |
| d. | $\underset{\underset{H}{\mid}}{\overset{OCO_2PNB}{-C-CF_3}}$ | 2-pyridyl | H |
| e. | $\underset{\underset{\underset{CO_2PNB}{\mid}}{-CH_2CH\phi}}{OCO_2PNB}$ | 2-furyl | OCH₃ |
| f. | $\underset{\underset{H}{\mid}}{\overset{OCO_2PNB}{-CCH_3}}$ | 2-thienyl | OCH₃ |
| g. | $\underset{\underset{-CH_2}{\mid}}{OCO_2PNB}$ | $-CH_2-\phi$ | OCH₃ |
| h. | H | " | H |
| i. | $\overset{OCO_2PNB}{\underset{S}{\diagdown}}$ (thienyl-OCO₂PNB group) | " | H |
| j. | $\underset{\underset{\underset{HNCO_2PNB}{\mid}}{-CHCH_2CH\phi}}{OCO_2PNB}$ | " | H |
| k. | $-CH_2OCPNB$ (with =O) | $-CH_2CH_2OCCH$ (with =O) | H |
| l. | $-CH_2OCPNB$ (with =O) | $-CH_2CH_2OSi(CH_3)_2C(CH_3)_3$ | H |

PNB = p-nitrobenzyl
φ = phenyl

EXAMPLE 13

Preparation of secolactam 3

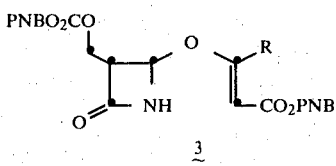

R = phenyl

To a stirred mixture of 33.8 mg (0.1 mmol) of azetidinones 1 and 29.9 mg (0.1 mmol) of 2 in 2.0 ml tetrahydrofuran at 25° C. is added 22.5 (0.11 mmol) of aluminum isopropoxide. The mixture is stirred at 25° C. under a nitrogen atmosphere for 60 hours. The solvent is removed by evaporation and the residue is partitioned between ethyl acetate and cold dilute aqueous HCl. The EtOAc phase is separated, washed with brine, dried with MgSO₄, filtered, and evaporated. The secolactam 3 is obtained by plate layer chromatography.

EXAMPLE 14

Employing the procedures described in the foregoing text and Examples, the following azetidinones 3 are prepared by analogy:

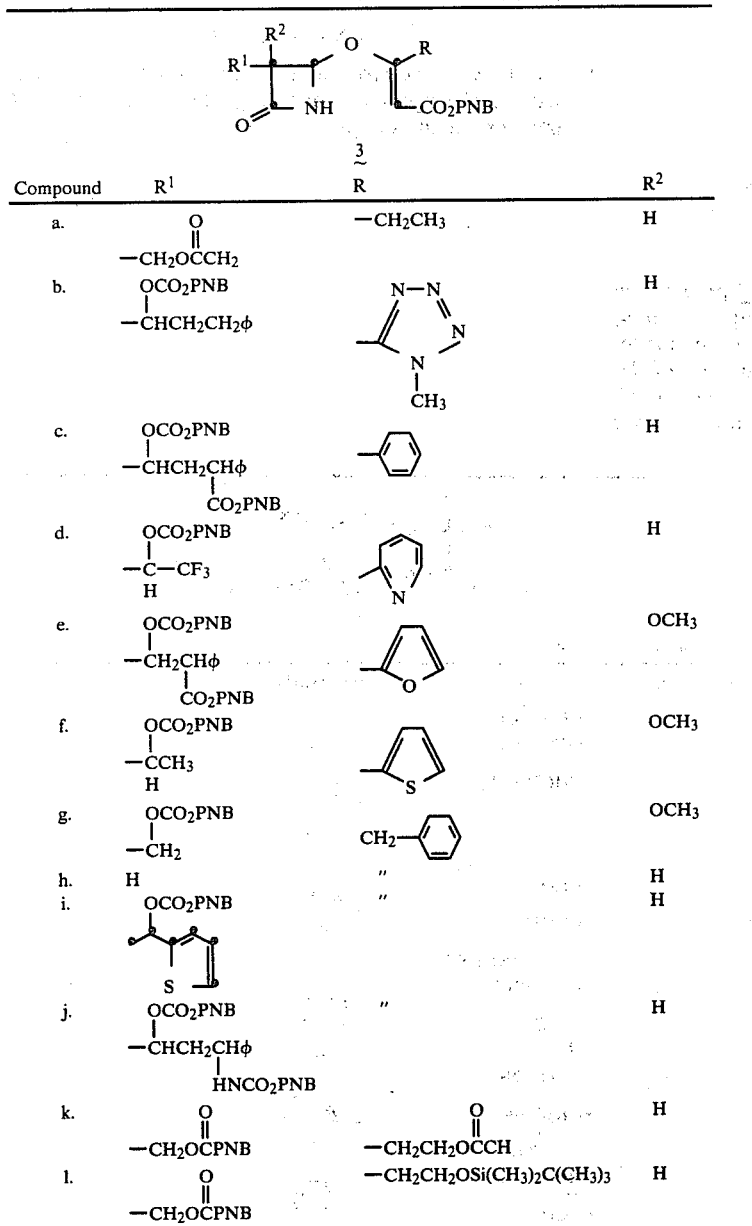
PNB = p-nitrobenzyl
φ = phenyl
EXAMPLE 15
Preparation of 4, R₁=R₂=H, R₃=CH₃,
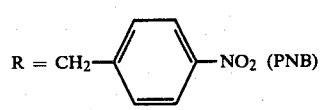
Reaction:
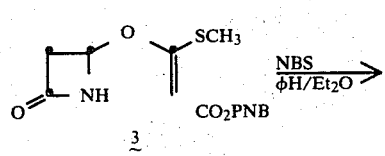
-continued
To a stirred mixture of 60.8 mg (0.18 mmol) of 3 in 2 ml tetrahydrofuran and 32.3 mg (0.18 mmol) HMPA is added 35.6 mg (0.2 mmol) of solid N-bromosuccinimide. The mixture is stirred at room temperature for 16 hrs. The mixture is evaporated and quickly purified by plate layer chromatography to provide 4.

EXAMPLE 16

Preparation of bromide 4

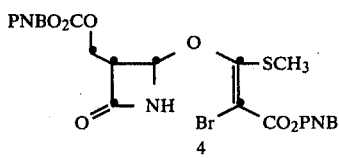

PNB = p-nitrobenzyl

To a stirred solution of the secolactam 3 prepared in Example 19 (54.7 mg 0.1 mmol) and 17.9 mg (0.1 mmol) of hexamethylphosphoramide in 2 ml dry tetrahydrofuran at 25° C. is added 17.8 mg (0.1 mmol) of N-bromosuccinimide. The mixture is stirred at 25° C. under $N_2$ for 23 hr. and the solvent is removed under reduced pressure. Purification by repetitive plate layer chromatography affords bromide 4.

EXAMPLE 17

Following the procedures described in the foregoing text and Examples, the following intermediate species 4 are representatively prepared by analogy.

| Compound | $R^1$ | R | $R^2$ |
|---|---|---|---|
| a. | —CH₂OC(O)CH₂ | —CH₂CH₃ | H |
| b. | —CH(OCO₂PNB)CH₂CH₂φ | 1-methyl-tetrazol-5-yl | H |
| c. | —CH(OCO₂PNB)CH₂CHφ(CO₂PNB) | phenyl | H |
| d. | —C(OCO₂PNB)(H)CF₃ | 2-pyridyl | H |
| e. | —CH(OCO₂PNB)CH₂φ(CO₂PNB) | 2-furyl | OCH₃ |
| f. | —C(OCO₂PNB)(H)CH₃ | 2-thienyl | OCH₃ |
| g. | —CH(OCO₂PNB)CH₂ | —CH₂-phenyl | OCH₃ |
| h. | H | " | H |
| i. | OCO₂PNB-substituted thienyl | " | H |
| j. | —CH(OCO₂PNB)CH₂CHφ(HNCO₂PNB) | " | H |
| k. | —CH₂OC(O)PNB | —CH₂CH₂OC(O)CH | H |
| l. | —CH₂OC(O)PNB | —CH₂CH₂OSi(CH₃)₂C(CH₃)₃ | H |

PNB = p-nitrobenzyl
φ = phenyl

EXAMPLE 18

Preparation of bromide 4

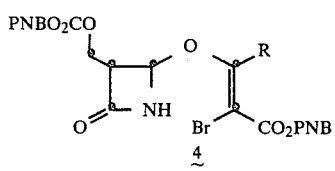
4

PNB = p-nitrobenzyl
R = phenyl

To a stirred mixture of the secolactam derivative 3 of Example 21 (57.7 mg, 0.1 mmol) and 17.9 mg (0.1 mmol) of hexamethylphosphoramide in 2 ml dry tetrahydrofuran at 25° C. is added 17.8 mg (0.1 mmol) of N-bromosuccinimide. The mixture is stirred at 25° C. under $N_2$ for 12 hours and the solvent removed under reduced pressure. Purification by repetitive plate layer chromatography provides bromide 4.

EXAMPLE 19

Following the procedure described in the foregoing text and Examples, the following bromides 4 are representatively obtained:

| Compound | R¹ | R | R² |
|---|---|---|---|
| a. | —CH₂OC(O)CH₂ | —CH₂CH₃ | H |
| b. | —CH(OCO₂PNB)CH₂CH₂φ | 1-methyl-1,2,3-triazol-4-yl | H |
| c. | —CH(OCO₂PNB)CH₂CHφ(CO₂PNB) | phenyl | H |
| d. | —C(OCO₂PNB)(H)CF₃ | 2-pyridyl | H |
| e. | —CH(OCO₂PNB)CH₂CHφ(CO₂PNB) | 2-furyl | OCH₃ |
| f. | —C(OCO₂PNB)(H)CH₃ | 2-thienyl | OCH₃ |
| g. | —CH(OCO₂PNB)CH₂— | —CH₂—phenyl | OCH₃ |
| h. | H | " | H |
| i. | —CH(OCO₂PNB)— (thienyl system) | " | H |
| j. | —CH(OCO₂PNB)CH₂CHφ(HNCO₂PNB) | " | H |
| k. | —CH₂OC(O)PNB | —CH₂CH₂OC(O)CH | H |
| l. | —CH₂OC(O)PNB | —CH₂CH₂OSi(CH₃)₂C(CH₃)₃ | H |

PNB = p-nitrobenzyl
φ = phenyl

EXAMPLE 20

Preparation of 5: $R_1=R_2=H$, $R_3=Me$,

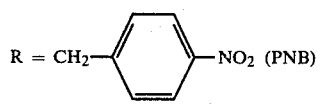

Reaction:

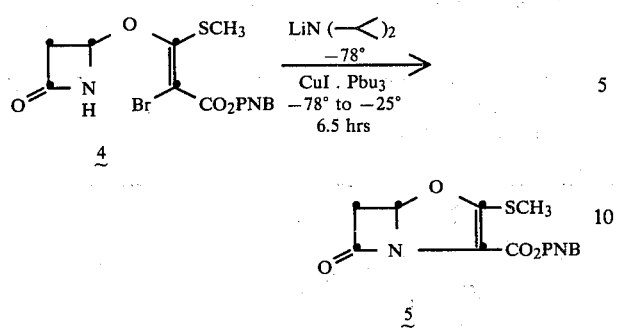 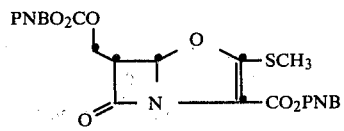

To a stirred solution of bromolactam 4 (50 mg, 0.12 mmol) and 46.0 mg (0.12 mmol) of cuprous iodide-tri-n-butylphosphine complex in 15 ml dry THF at −78° under Argon atmosphere is added dropwise a cold solution of freshly prepared lithium diisopropylamide (0.12 mmol) in 6.6 ml dry THF. The resulting greenish solution is stirred from −78° C. to −25° C. under Argon atmosphere over a period of 6.5 hrs. The reaction is quenched at −25° C. with 1.0 ml saturated NH₄Cl (aq) solution and is then partitioned between Et₂O/H₂O. The organic phase is separated and washed successively with aqueous NH₄Cl solution and brine, then dried MgSO₄, filtered, and evaporated. The residue is purified by plate layer chromatography to provide 5.

EXAMPLE 21

Preparation of Oxapenem 5

To a stirred mixture of the seco lactam bromide 4 of Example 23 (62.6 mg, 0.1 mmol) and cuprous bromidedimethylsulfide complex (67.7 mg, 0.33 mmol) in 10 ml dry tetrahydrofuran at −78° C. under a nitrogen atmosphere is added a cold, freshly prepared solution of lithium diisopropylamide (0.11 mmol) in 4 ml dry tetrahydrofuran. The mixture is stirred at −78° C. for 40 minutes and is allowed to warm to 0° C. over a period of 5 hours. At 0° C., 2 ml of saturated ammonium chloride (aq.) solution is added and the mixture is partitioned between ether and water. The organic phase is separated and washed further with saturated ammonium chloride solution and brine. The organic phase is separated, dried over MgSO₄, filtered, and evaporated. Purification is accomplished by plate layer chormatography to yield oxapenem 5.

EXAMPLE 22

Following the procedure described in the foregoing Examples and text, there is obtained the following representative penems 5 by analogy:

| Compound | R¹ | R | R² |
|---|---|---|---|
| a. | —CH₂OCCH₂ (O) | —CH₂CH₃ | H |
| b. | —CHCH₂CH₂φ \| OCO₂PNB | triazole N—N / N-CH₃ | H |
| c. | —CHCH₂CHφ \| OCO₂PNB \| CO₂PNB | phenyl | H |
| d. | —C—CF₃ \| OCO₂PNB \| H | pyridyl | H |
| e. | —CH₂CHφ \| OCO₂PNB \| CO₂PNB | tetrahydrofuryl | OCH₃ |
| f. | —CCH₃ \| OCO₂PNB \| H | thienyl | OCH₃ |
| g. | —CH₂ \| OCO₂PNB | CH₂—phenyl | OCH₃ |
| h. | H | " | H |

-continued structure 5: β-lactam with R², R¹ on C3, O-linked to C=C(R)(CO₂PNB)

| Compound | R¹ | R | R² |
|---|---|---|---|
| i. | OCO₂PNB-CH(-)-C(CH₃)=CH-S- (cyclic thiophene-like substituent with OCO₂PNB) | " | H |
| j. | -CH(OCO₂PNB)CH₂CHφ(HNCO₂PNB) | " | H |
| k. | -CH₂OC(O)PNB | -CH₂CH₂OC(O)CH | H |
| l. | -CH₂OC(O)PNB | -CH₂CH₂OSi(CH₃)₂C(CH₃)₃ | H |

PNB = p-nitrobenzyl
φ = phenyl structure 4: β-lactam with R², R¹ on C3, NH, O-linked to C(SR)=C(Br)(CO₂PNB)

| Compound | R¹ | R | R² |
|---|---|---|---|
| a. | -CH₂OC(O)CH₂ | -CH₂CH₃ | H |
| b. | -CH(OCO₂PNB)CH₂CH₂φ | 1-methyl-tetrazol-5-yl | H |
| c. | -CH(OCO₂PNB)CH₂CHφ(CO₂PNB) | phenyl | H |
| d. | -CH(OCO₂PNB)CF₃ | 2-pyridyl (methylpyridine) | H |
| e. | -CH(OCO₂PNB)CH₂φ(CO₂PNB) | 2-furyl | OCH₃ |
| f. | -CH(OCO₂PNB)CH₃ | 2-thienyl | OCH₃ |
| g. | -CH(OCO₂PNB)CH₂ | -CH₂φ | OCH₃ |
| h. | H | " | H |
| i. | OCO₂PNB-CH(-)-C(CH₃)=CH-S- | " | H |
| j. | -CH(OCO₂PNB)CH₂CHφ(HNCO₂PNB) | " | H |

-continued

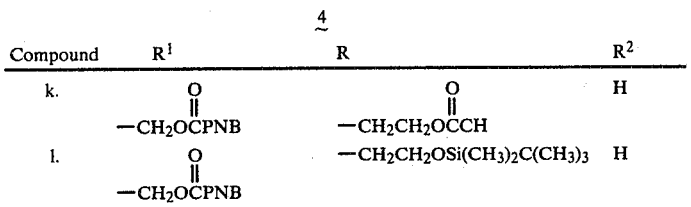

| Compound | R[1] | R | R[2] |
|---|---|---|---|
| k. | —CH$_2$OCPNB (C=O) | —CH$_2$CH$_2$OCCH (C=O) | H |
| l. | —CH$_2$OCPNB (C=O) | —CH$_2$CH$_2$OSi(CH$_3$)$_2$C(CH$_3$)$_3$ | H |

PNB = p-nitrobenzyl
φ = phenyl

EXAMPLE 23

Conversion of 5 (R$_1$=R$_2$=H, R$_3$=CH$_3$,

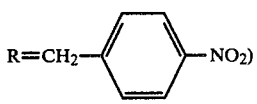

R=CH$_2$—⟨phenyl⟩—NO$_2$)

to the free acid and its sodium salt. I

Reaction:

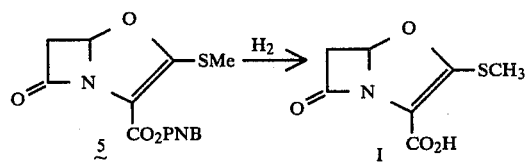

A mixture of 6.7 mg (0.02 mmol) of oxapenem 5 and 7.8 mg 10% Pd/C in 1.0 ml dioxane, 1.0 ml THF, 0.5 ml H$_2$O, and 0.5 ml 0.5 N pH 7 phosphate buffer is hydrogenated at rt and 40 psi for 25 min. The catalyst is removed by filtration through SOLKA-FLOC washing with water. The filtrate is extracted with an equal volume of EtOAc and the aqueous layer is then assayed for antibacterial activity. The aqueous solution is then cooled on an ice/H$_2$O bath and is acidified to pH 3.3 with 1.0 M pH 2 phosphate buffer. The solution is extracted twice with EtOAc and the extract is dried over MgSO$_4$, filtered, and evaporated to provide I. The residue is dissolved in CHCl$_3$; the chloroform solution is quickly evaporated and is redissolved in a minimum amount of acetone and is then treated with an equivalent amount of NaHCO$_3$ in 0.5 ml H$_2$O. The Me$_2$CO is removed under reduced pressure and the aqueous phase is lyophilized to give a quantitative yield of sodium salt of I.

EXAMPLE 24

Preparation of Oxapenem I

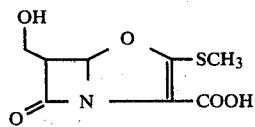

A mixture of 10 mg of 10% palladium on carbon, 4.7 mg. (0.0086 mmol) of the oxapenem of Example 21 and 1 mg. sodium bicarbonate in 0.8 ml ethylacetate, 0.2 ml isopropanol, and 0.5 ml of 0.5 M pH 7 phosphate buffer is hydrogenated at 40 psi at 25° C. in a Parr shaker for 48 minutes. The catalyst is removed by filtration through supercel and is washed thoroughly with deionized water. The cold filtrate is extracted with ethylacetate and the separated aqueous phase is acidified at 0° C. with 0.1 M pH 2 phosphate buffer to pH 2.5. The aqueous phase is extracted thoroughly with EtOAc. The extracts are combined, dried over anhydrous sodium sulfate, filtered and evaporated to provide oxapenem I.

The free acid is converted to the corresponding sodium salt by treatment with an equivalent amount of an aqueous acetone solution of sodium bicarbonate, followed by removal of the acetone under reduced pressure and lyophilization of the aqueous solution.

EXAMPLE 25

Following the procedures set out in the foregoing Examples and text, the following species of the present invention are obtained by analogy. In the table Me=methyl, and φ=phenyl.

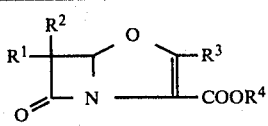

| Compound | R[1] | R[2] | R[3] | R[4] |
|---|---|---|---|---|
| 1. | CH$_2$OH | H | SCH$_2$CH$_2$NH$_2$ | H |
| 1a. | CH(OH)CH$_3$ | H | SCH$_2$CH$_2$NH$_2$ | H |
| 2. | CH$_2$OH | OMe | SCH$_2$NH$_2$ | H |

-continued $$\underset{O}{\overset{R^2}{\underset{|}{R^1-}}}\overset{O}{\underset{N}{\bigsqcup}}\overset{R^3}{\underset{COOR^4}{\rightleftharpoons}} \quad I$$

| Compound | $R^1$ | $R^2$ | $R^3$ | $R^4$ |
|---|---|---|---|---|
| 3. | HC(OH)CH$_3$ | OMe | ![tetrazole-SCH$_3$] S—C(=N-N=N-N(CH$_3$)) | Na |
| 4. | HC(OH)CH$_2$CH$_3$ | H | SCH$_2$CH$_2$NH$_2$ | H |
| 5. | $\phi$CH$_2$CH$_2$CH(OH) | H | —C$_6$H$_4$—OCH$_3$ | Na |
| 6. | HC(OH)CH$_3$ | OMe | thienyl (S) | Na |
| 7. | CH$_2$OH | H | furyl (O) | CH$_2$OCCMe$_3$ (O=) |
| 8. | (CH$_3$)$_2$C(OH) | OMe | SCH$_2\phi$ | Na |
| 9. | CF$_3$CH$_2$CH(OH) | H | pyridyl (N) | Na |
| 10. | $\phi$CHCH$_2$CH(OH) with NH$_2$ | H | —C$_6$H$_4$—SCF$_3$ | H |
| 11. | CH$_2$OH | H | thiadiazole (N—N, S) | Na |
| 12. | (CH$_3$)$_2$CH—CH(OH) | H | SCH$_2$CH$_2$NH$_2$ | H |
| 13. | $\phi$CHCH with OH and NH$_2$ | OMe | S—CH$_2$-thienyl | H |
| 14. | $\phi$—CH$_2$CH$_2$CH with NH$_2$ and OH | H | SCH$_2$—C(=N-N=N-N(CH$_3$)) | H |

EXAMPLE 26

Preparation of Pharmaceutical Compositions

One such unit dosage form consists in mixing 120 mg. of 6-hydroxymethyl-2-aminoethylthio-oxapen-2-em-3-carboxylic acid with 20 mg. of lactose and 5 mg of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 6-hydroxymethymethyl-2-aminoethylthio-oxa-Pen-2-em-3-carboxylic acid | 125 mg. |
| Dicalcium Phosphate | 192 mg. |
| Cornstarch, U.S.P. | 6 mg. |
| Lactose, U.S.P. | 190 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

PARENTERAL SOLUTION

| Ampoule: | |
|---|---|
| 6-(1'-hydroxyethyl-2-methylthio-oxa-Pen-2-em-3-carboxylic acid | 500 mg. |
| Diluent: Sterile Water for Injection | 2 cc |

OPHTHALMIC SOLUTION

| | |
|---|---|
| 6-hydroxymethyl-2-aminoethylthio-oxa-Pen-2-em-3-carboxylic acid | 100 mg |
| Hydroxypropylmethyl cellulose | 5 mg |
| Sterile Water | to 1 ml. |

OPTIC SOLUTION

| | | |
|---|---|---|
| 6-hydroxymethyl-2-aminoethylthio-oxa-Pen-2-em-3-carboxylic acid | | 100 mg |
| Benzalkonium chloride | | 0.01 mg |
| Sterile Water | to | 1 ml. |

TOPICAL OINTMENT

| | |
|---|---|
| 6-hydroxymethyl-2-aminoethylthio-oxa-Pen-2-em-3-carboxylic acid | 100 mg |
| Polyethylene Glycol 4000 U.S.P. | 400 mg |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

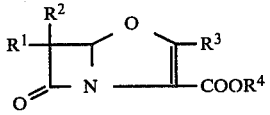

wherein:

R$^4$ is hydrogen, pharmaceutically acceptable salts, or benzyl, p-nitrobenzyl, o-nitrobenzyl, t-butyl, bromo-t-butyl, t-butyl-dimethylsilyl, trimethylsilyl, trichloroethyl, pivaloyloxymethyl, allyl, methallyl, (2-methylthio)ethyl, or 3-buten-1-yl;

R$^1$ and R$^2$ are independently selected from: hydrogen, hydroxymethyl, 1-hydroxyethyl, 1-hydroxy-3-phenylpropyl, 1-hydroxy-3-phenyl-3-carboxypropyl, 1-hydroxy-2,2,2-trifluoroethyl, methoxyl, phenyl, methyl, 2-thienyl, 2-pyridyl, benzyl, p-methoxyphenyl; and R$^3$ is —SCH$_2$CH$_3$
—SCH$_3$
—S(CH$_2$)$_n$NH$_2$ (n=1—5)

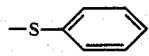

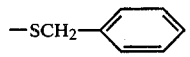

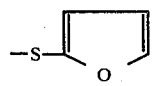

—SCH$_2$CH$_2$OCCH$_3$ (with O double-bonded to C)

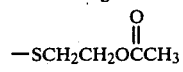

—CH$_3$

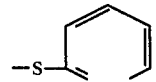

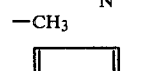

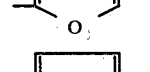

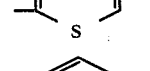

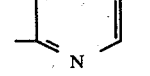

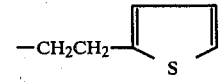

—OCH$_3$

—NHCH$_2$CH$_3$; except that when both R$^1$ and R$^2$ are hydrogen, R$^3$ cannot be methyl; and, except that R$^3$ cannot be —SCH$_2$CH$_2$NH$_2$ when R$^2$ is hydrogen and R$^1$ is 1-hydroxyethyl.

2. The compound according to claim 1 wherein R$^2$ is hydrogen.

3. The compound of claim 2 wherein R$^1$ is 1-hydroxyethyl.

4. The compound of claim 2 wherein R$^1$ is hydroxy methyl.

5. An antibiotic pharmaceutical composition comprising in unitary dosage form, an antibacterially effective amount of a compound according to claim 1 and a pharmaceutically acceptable carrier therefor.

* * * * *